United States Patent [19]

Patterson et al.

[11] Patent Number: 5,918,283
[45] Date of Patent: Jun. 29, 1999

[54] COATING FOR THERMOELASTICITY

[75] Inventors: Eann Alexander Patterson; Sandro Barone, both of Sheffield, United Kingdom

[73] Assignee: The University of Sheffield, Sheffield, United Kingdom

[21] Appl. No.: 08/910,051

[22] Filed: Aug. 12, 1997

[30] Foreign Application Priority Data

Aug. 20, 1996 [GB] United Kingdom .................. 9617435

[51] Int. Cl.⁶ ..................................................... G01L 1/24
[52] U.S. Cl. ............................................... 73/800; 73/762
[58] Field of Search ............................. 73/800, 808, 762, 73/801

[56] References Cited

U.S. PATENT DOCUMENTS

| | | |
|---|---|---|
| 3,718,065 | 2/1973 | Liber . |
| 3,994,598 | 11/1976 | Reytblatt . |
| 4,008,960 | 2/1977 | Reytblatt . |
| 4,378,701 | 4/1983 | Mountain et al. ........................ 73/808 |
| 4,541,059 | 9/1985 | Toshihiko .................................. 73/808 |
| 4,713,540 | 12/1987 | Gilby et al. ............................... 73/800 |
| 4,914,487 | 4/1990 | Croizer et al. ............................ 356/35 |
| 5,201,582 | 4/1993 | Lesniak ..................................... 73/808 |
| 5,347,128 | 9/1994 | Puram et al. . |
| 5,693,889 | 12/1997 | Nadolink ................................... 73/800 |

OTHER PUBLICATIONS

*Optical Properties*, vol. 10, pp. 503–519.

*Primary Examiner*—Max H. Noori
*Attorney, Agent, or Firm*—Trexler, Bushnell, Giangiorgi & Blackstone, Ltd.

[57] ABSTRACT

A first aspect of the invention relates to an epoxy resin coating used in reflection photoelasticity, which is "black" in the infra-red part of the spectrum; another aspect to the use of an epoxy resin as a coating on at least one surface of a body to be subjected to cyclic loading and examined by thermoelasticity, and another aspect to a method of making thermoelastic measurements of a body when subjected to cyclic loading and hence measurements of stresses or strains, comprising, as an initial step, coating the surface(s) of the body to be measured with an epoxy resin whereby the surface(s) so coated represents a black body.

3 Claims, No Drawings

COATING FOR THERMOELASTICITY

BACKGROUND OF THE INVENTION

1. Field of the Invention

When a solid body is subjected to cyclic loading it undergoes a cyclic variation in temperature. The variation in temperature is a function of the variation in the sum of the principal stress or strain experienced by the body. The temperature changes can be measured using a sensitive infra-red detector.

2. Descriptions of the Prior Art

Two measuring systems are commercially available; one, SPATE (Trade Mark) uses a scanning device to assemble a full-field picture during a large number of cycles. The second and more modem device, DELTATHERM (Trade Mark) uses an array of diodes to record a full-field image during a small number of cycles. It is recommended that a black coating is used on the component with both devices. The primary reason for the use of the coating is to provide a surface of uniform emissivity, and the use of black converts the component into a 'black body' thus maximising the emitted infra-red signal. The coating in common use by thermoelasticians is a spray-on black paint.

OBJECT OF THE INVENTION

A basic object of the present invention is to provide an improved coating for thermoelastic measurements and, if required, for simultaneous photoelastic measurement.

SUMMARY OF THE INVENTION

According to a first aspect of the present invention there is provided, an epoxy resin coating used in reflection photoelasticity, which coating is 'black' in the infra-red part of the spectrum.

Another aspect of the invention is directed to the use of an epoxy resin as a coating on at least one surface of a body to be subjected to cyclic loading and examined by reflection thermoelasticity.

Another aspect of the invention concerns a method of making thermoelastic measurements of a body when subjected to cyclic loading comprising, as an initial step, coating the surface(s) of the body to be measured with an epoxy resin, whereby the surface(s) so coated represents a black body.

The various aspects of the invention are based upon the discovery that epoxy resin is "black" in the infra-red part of the spectrum, and is thereof usable as a surface coating in reflection thermoelasticity. This can be demonstrated when a thin sheet of epoxy resin is placed between an infra-red detector and a component subject to cyclic loading. The component is completely hidden from the detector both when the epoxy is transparent to the visible spectrum, and when it is sprayed with black paint.

Further, when the coating is bonded to the body (e.g. an engineering component), to be investigated by reflection photoelasticity, it acts as a witness to the surface strains subsequently induced in the body. The changes in the surface strains can be monitored using an infra-red detector. The signal is found to be of a similar strength and nature to that observed when a black coating is painted onto the body.

The method of affixing the epoxy resin to the body is not important providing a bond is created that is strong enough to transfer the strains without disturbance. The creation of an epoxy resin coating by spraying onto the surface(s) of the body is not excluded. The particular type of epoxy resin is not important, but it is advantageous for resin to be transparent in the visible spectrum so that it can be used for reflection photoelasticity. It is also advantageous for it to have a low modulus of elasticity so that it does not significantly reinforce the body and hence disturb the surface strain distribution.

When such a coating in accordance with the various aspects of the invention is applied to the body and the body is loaded cyclically, a thermoelastic instrument and a photoelastic instrument can be simultaneously used to record the sum and the difference of the principal stresses. The resulting data can be combined to evaluate the individual principal stresses. The direction of the stresses is can be obtained from the photoelastic instrument. This data can be obtained for a full-field of view using instruments such as a DELTATHERM (Trade Mark) system for thermoelasticity and an optical collector head for photoelasticity. When the instruments are to be used simultaneously, it is recommended that the light source of the photoelastic instrument should have a bandwidth filter to remove all incident infra-red emissions. In addition, it is recommended that the thermoelastic and photoelastic instrument should view the body using a common optical path that incorporates a device for splitting the infra-red and visible emissions, such as a 'hot mirror'. In this manner the view observed in the visible spectrum by the photoelastic detector is identical to that observed in the infra-red spectrum by the thermoelastic detector. This facilitates the combination of the data.

We claim:

1. A method of recording the sum and the difference of the principal stresses in a cyclically loaded body having a polymer coating bonded thereto, which coating is "black" in the infra-red part of the spectrum, and also which is transparent in the visible spectrum, comprising simultaneously using a thermoelastic instrument and photoelastic instrument to monitor the polymer coating and measure both thermoelastic and photoelastic signals relating to the principal stresses in the cyclically loaded body, whereby said coating permits simultaneous measurement of both thermoelastic and photoelastic signals.

2. A method as claimed in claim 1, wherein the coating is sprayed onto the at least one surface of the body to be investigated.

3. A method as claimed in claim 1, wherein the coating is an epoxy resin.

* * * * *